(12) United States Patent
Eto et al.

(10) Patent No.: US 10,973,501 B2
(45) Date of Patent: Apr. 13, 2021

(54) ENDOSCOPIC TREATMENT TOOL AND HANDLE

(71) Applicant: OLYMPUS CORPORATION, Tokyo (JP)

(72) Inventors: Hirofumi Eto, Tokyo (JP); Yasuhiko Kikuchi, Sagamihara (JP); Katsuji Uemichi, Tokyo (JP); Masatoshi Tonomura, Tokyo (JP); Jin Hiraoka, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 315 days.

(21) Appl. No.: 16/144,042

(22) Filed: Sep. 27, 2018

(65) Prior Publication Data

US 2019/0021708 A1    Jan. 24, 2019

Related U.S. Application Data

(63) Continuation of application No. PCT/JP2016/061041, filed on Apr. 4, 2016.

(51) Int. Cl.
*A61B 10/04* (2006.01)
*A61B 1/00* (2006.01)
(Continued)

(52) U.S. Cl.
CPC ............... *A61B 10/04* (2013.01); *A61B 1/00* (2013.01); *A61B 10/0283* (2013.01);
(Continued)

(58) Field of Classification Search
CPC .......... A61B 10/04; A61B 1/00; A61B 17/34; A61B 10/0283; A61B 8/12; A61B 2010/0208; A61B 1/00133
See application file for complete search history.

(56) References Cited

U.S. PATENT DOCUMENTS 8,197,396 B2 * 6/2012 Hiraoka ................. A61B 10/06
600/104

FOREIGN PATENT DOCUMENTS

JP    2001-037765 A        2/2001
JP    2001037765 A   *   10/2001
(Continued)

OTHER PUBLICATIONS

Notice of Allowance dated Jun. 25, 2019 recieved in Japanese Patent Application No. 2018-510031.
(Continued)

*Primary Examiner* — Michael J Carey
*Assistant Examiner* — Tadios E Molla
(74) *Attorney, Agent, or Firm* — Scully, Scott, Murphy & Presser, P.C.

(57) ABSTRACT

An endoscopic treatment tool includes a sheath; a treatment portion capable of protruding and retracting from a distal end of the sheath; a manipulation main body; a slider which advances and retracts in a longitudinal axis direction to cause the treatment portion to protrude and retract from the sheath; a first locking mechanism which locks the slider at a position at which the distal end of the treatment portion is accommodated in the sheath in accordance with a retracting manipulation of the slider; a second locking mechanism provided at further distal side than the first locking mechanism and restricts advance of the slider by being locked to the manipulation main body; a fixing mechanism provided in the second locking mechanism and fixed to the manipulation main body by sliding; and a restricting portion which restricts fixing of the fixing mechanism to the manipulation main body.

14 Claims, 10 Drawing Sheets

(51) Int. Cl.
*A61B 17/34* (2006.01)
*A61B 10/02* (2006.01)
*A61B 8/12* (2006.01)

(52) U.S. Cl.
CPC ................ *A61B 17/34* (2013.01); *A61B 8/12* (2013.01); *A61B 2010/0208* (2013.01)

(56) References Cited

FOREIGN PATENT DOCUMENTS

| JP | 2010-269126 A | 12/2010 |
|----|---------------|---------|
| WO | 2014/132672 A1 | 9/2014 |
| WO | 2014/132673 A1 | 9/2014 |
| WO | WO 2015/076154 A1 | 5/2015 |
| WO | 2016/021269 A1 | 2/2016 |
| WO | WO 2016/042849 A1 | 3/2016 |

OTHER PUBLICATIONS

International Search Report dated May 31, 2016 issued in PCT/JP2016/061041.

* cited by examiner

ENDOSCOPIC TREATMENT TOOL AND HANDLE

This application is a continuation application based on PCT Patent Application No. PCT/JP2016/061041, filed Apr. 4, 2016, the content of which is incorporated herein by reference.

BACKGROUND OF THE INVENTION

Field of the Invention

The present invention relates to an endoscopic treatment tool and handle.

Description of the Related Art

An inspection method called a biopsy, in which a small amount of living tissue is collected and observed with a microscope, is known. In a biopsy that uses a puncture needle consisting of a needle tube, for example, after bringing an endoscope insertion portion close to an examination target part, a sheath accommodating the puncture needle is caused to protrude from a treatment tool channel. Next, by manipulating a manipulating unit provided on a proximal end side of the puncture needle under ultrasonic observation, the puncture needle is caused to protrude from the sheath and puncture the examination target part, the living tissue is collected in the puncture needle, and the puncture needle is retracted into the sheath and extracted from the body.

Japanese Unexamined Patent Application, First Publication No. 2001-037765 discloses the endoscopic puncture device having a structure which has an automatic puncture function for protruding the puncture needle at a high speed, and includes a switch mechanism capable of switching between a restricted state that prevents the operation of the automatic puncture function until a distal end of the puncture needle is disposed at a predetermined position and a restriction release state that allows protruding of the puncture needle.

In the endoscopic puncture device of Japanese Unexamined Patent Application, First Publication No. 2001-037765, a sheath capable of being inserted into the treatment tool channel of the insertion portion of the endoscope is disposed outside the puncture needle in order to prevent an inner surface of the treatment tool channel from being damaged by the sharp distal end of the puncture needle.

When the puncture needle advances and retracts in the treatment tool channel, the distal end of the puncture needle is required to be accommodated in the sheath. The endoscopic puncture device of Japanese Unexamined Patent Application, First Publication No. 2001-037765 has a structure that temporarily fixes a needle slider when the needle slider is manipulated to retract until the distal end of the puncture needle is accommodated in the sheath.

SUMMARY OF THE INVENTION

An endoscopic treatment tool according to a first aspect of the present invention includes a sheath inserted into a treatment tool insertion channel of an endoscope; a treatment portion which is inserted into the sheath and is capable of protruding from and retracting into a distal end of the sheath; a manipulation main body fixed to a proximal end of the sheath and formed along a longitudinal axis of the sheath; a slider advancing and retracting in a longitudinal axis direction with respect to the manipulation main body to cause the treatment portion to protrude from and retract into the sheath; a first locking mechanism which locks the slider with a first amount of force at a position at which a distal end of the treatment portion is accommodated in the sheath in accordance with a retracting manipulation of the slider; a second locking mechanism which is provided at further distal side than the first locking mechanism, is capable of advancing and retracting in the longitudinal axis direction with respect to the manipulation main body, the second locking mechanism being locked to the manipulation main body with a second amount of force greater than the first amount of force, and restricts advance of the slider by abutting the slider; a fixing mechanism provided in the second locking mechanism and fixed to the manipulation main body by sliding with respect to the manipulation main body to fix a position of the second locking mechanism with respect to the manipulation main body; and a restricting portion which restricts fixing of the fixing mechanism to the manipulation main body.

A second aspect of the present invention is the endoscopic treatment tool according to the first aspect, wherein a distal end of the slider may abut the second locking mechanism in a state in which the slider is locked by the first locking mechanism.

A third aspect of the present invention is the endoscopic treatment tool according to the first or second aspect, wherein a first fixing portion may be formed on an outer peripheral surface of the manipulation main body at a distal end side of a region in which the slider advances and retracts, a second fixing portion may be formed on a proximal end side of the region, the second locking mechanism may be capable of being fixed by the fixing mechanism by allowing the sliding of the fixing mechanism through the first fixing portion and the second fixing portion, and the restricting portion may be positioned between the first fixing portion and the second fixing portion.

A fourth aspect of the present invention is the endoscopic treatment tool according to the third aspect, wherein the first fixing portion may be formed in a region in which the slider is located so that the distal end of the treatment portion protrudes from the distal end of the sheath, and the second fixing portion may be formed in a region in which the slider is located so that the distal end of the treatment portion is accommodated in the sheath.

A fifth aspect of the present invention is the endoscopic treatment tool according to the third aspect, wherein the first fixing portion and the second fixing portion may be formed by a plurality of concavities and convexities continuously disposed in the longitudinal axis direction, a claw which engages with the concavities and convexities by moving with respect to the concavities and convexities may be formed in the fixing mechanism, and the restricting portion of the manipulation main body may include an abutting surface protruding further outward in a radial direction of the manipulation main body than the concave portion of the concavities and convexities.

A sixth aspect of the present invention is the endoscopic treatment tool according to the first aspect, wherein the first locking mechanism may include a click mechanism which generates a click feeling when the slider is retracted to a position at which the slider is locked by the first locking mechanism.

A seventh aspect of the present invention is the endoscopic treatment tool according to the first aspect, wherein the slider may be fixed to the treatment portion and the slider may be provided in the manipulation main body.

A handle according to the eighth aspect of the present invention is the handle which is configured to be manipulated by an operator in an endoscopic treatment tool which includes a sheath which is inserted into a treatment tool insertion channel of an endoscope, and a treatment portion which is capable of protruding from and retracting into a distal end of the sheath, the handle comprising: a manipulation main body fixed to a proximal end of the sheath; a slider which is capable of advancing and retracting with respect to the manipulation main body to cause the treatment portion to protrude from and retract into the sheath; a first locking mechanism which locks the slider with a first amount of force at a position at which a distal end of the treatment portion is accommodated in the sheath in accordance with a retract manipulation of the slider; a second locking mechanism which is provided on a further distal side than the first locking mechanism and is capable of advancing and retracting in the longitudinal axis direction with respect to the manipulation main body, the second locking mechanism restricting a an advance of the slider by being locked to the manipulation main body with a second amount of force greater than the first amount of force; a fixing mechanism provided in the second locking mechanism and fixed to the manipulation main body by sliding with respect to the manipulation main body to fix a position of the second locking mechanism with respect to the manipulation main body; and a restricting portion which restricts fixing of the fixing mechanism to the manipulation main body.

A ninth aspect of the present invention is the handle according to the eighth aspect, wherein a distal end of the slider may abut the second locking mechanism in a state in which the slider is locked by the first locking mechanism.

A tenth aspect of the present invention is the handle according to the eighth aspect, wherein a first fixing portion may be formed on an outer peripheral surface of the manipulation main body at a distal end side of a region in which the slider advances and retracts, and a second fixing portion may be formed on a proximal end side thereof, the second fixing portion may be capable of being fixed by the fixing mechanism by allowing the sliding of the fixing mechanism through the first fixing portion and the second fixing portion, and the restricting portion may be formed between the first fixing portion and the second fixing portion.

An eleventh aspect of the present invention is the handle according to the tenth aspect, wherein the first fixing portion may be formed in a region in which the slider is located so that the distal end of the treatment portion protrudes from the distal end of the sheath, and the second fixing portion may be formed in a region in which the slider is located so that the distal end of the treatment portion is accommodated in the sheath.

A twelfth aspect of the present invention is the handle according to the tenth aspect, wherein the first fixing portion and the second fixing portion may be formed by a plurality of concavities and convexities continuously disposed in the longitudinal axis direction, a claw which engages with the concavities and convexities by moving with respect to the concavities and convexities may be formed in the fixing mechanism, and the restricting portion of the manipulation main body may include an abutting surface protruding further outward in a radial direction of the manipulation main body than the concave portion of the concavities and convexities.

A thirteenth aspect of the present invention is the handle according to the eighth aspect, wherein the first locking mechanism may include a click mechanism which generates a click feeling when the slider is retracted to a position at which the slider is locked by the first locking mechanism.

A fourteenth aspect of the present invention is the handle according to the eighth aspect, wherein the slider may be fixed to the treatment portion and the slider is provided in the manipulation main body.

DETAILED DESCRIPTION OF THE INVENTION

Hereinafter, an endoscopic treatment tool including a puncture needle (an aspiration biopsy needle) as an endoscopic treatment tool according to an embodiment of the present invention will be described with reference to the accompanying drawings.

Figure 1:
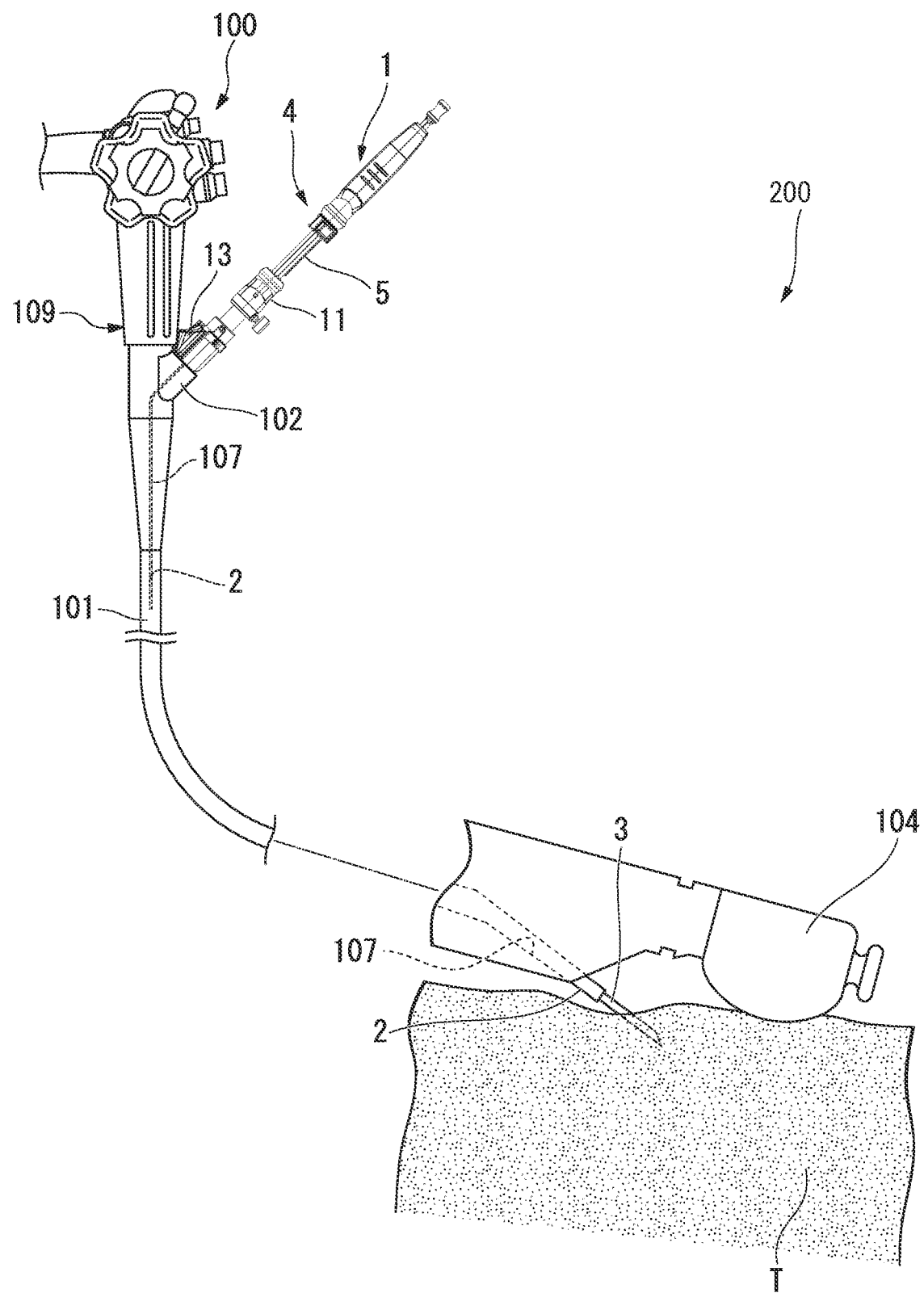
FIG. 1 is a schematic diagram illustrating a configuration of an endoscope system including an endoscopic treatment tool according to an embodiment of the present invention.

FIG. 1 is a schematic diagram illustrating a configuration of an endoscope system 200 including an endoscopic treatment tool 1 (hereinafter, referred to as a "treatment tool") according to an embodiment of the present invention. The treatment tool 1 according to the present embodiment used in a state that the treatment tool 1 is inserted into a treatment tool insertion channel (hereinafter, simply referred to as a "channel") 107 formed in an inserting portion 101 of an endoscope 100, and a holder 13 to be described later is fixed to a proximal end channel port 102 of the endoscope 100.

In the following description, a side positioned at a manipulating unit manipulated by the operator is referred to as a proximal end, and a side inserted into the body is referred to as a distal end. Further, in the description of each part, in some cases the term "central axis C" is used to include the central axis C of the manipulating unit and a longitudinal axis.

Figure 2:
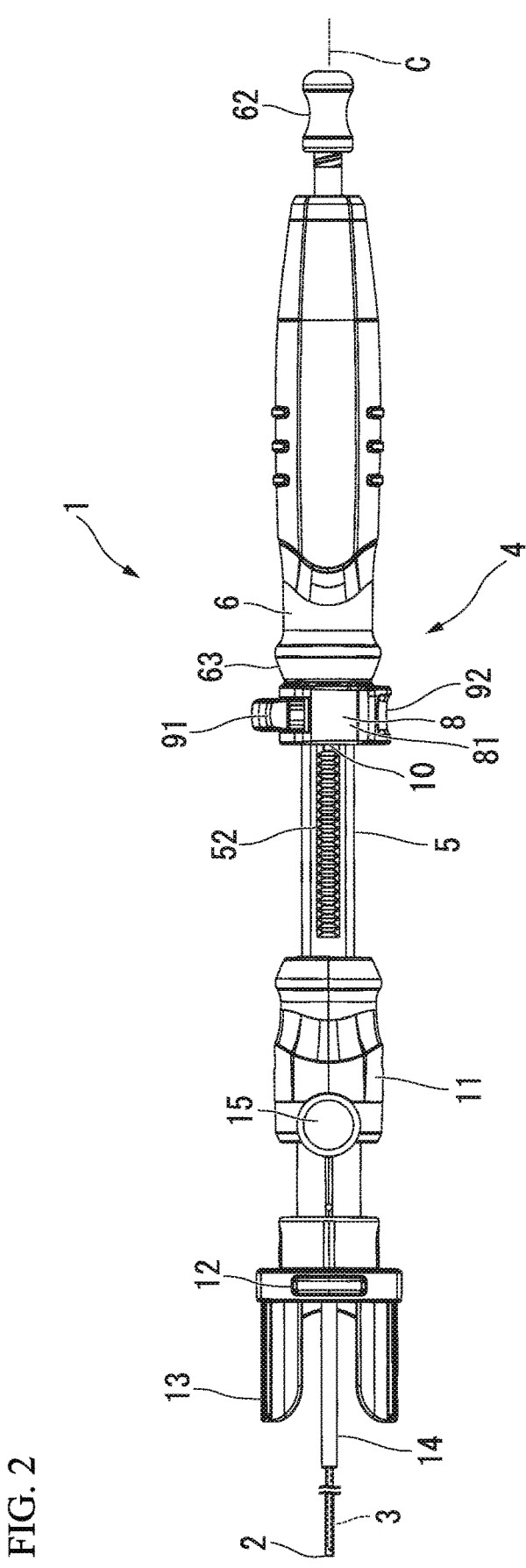
FIG. 2 is a bottom view illustrating the endoscopic treatment tool according to the embodiment of the present invention.
Figure 5:
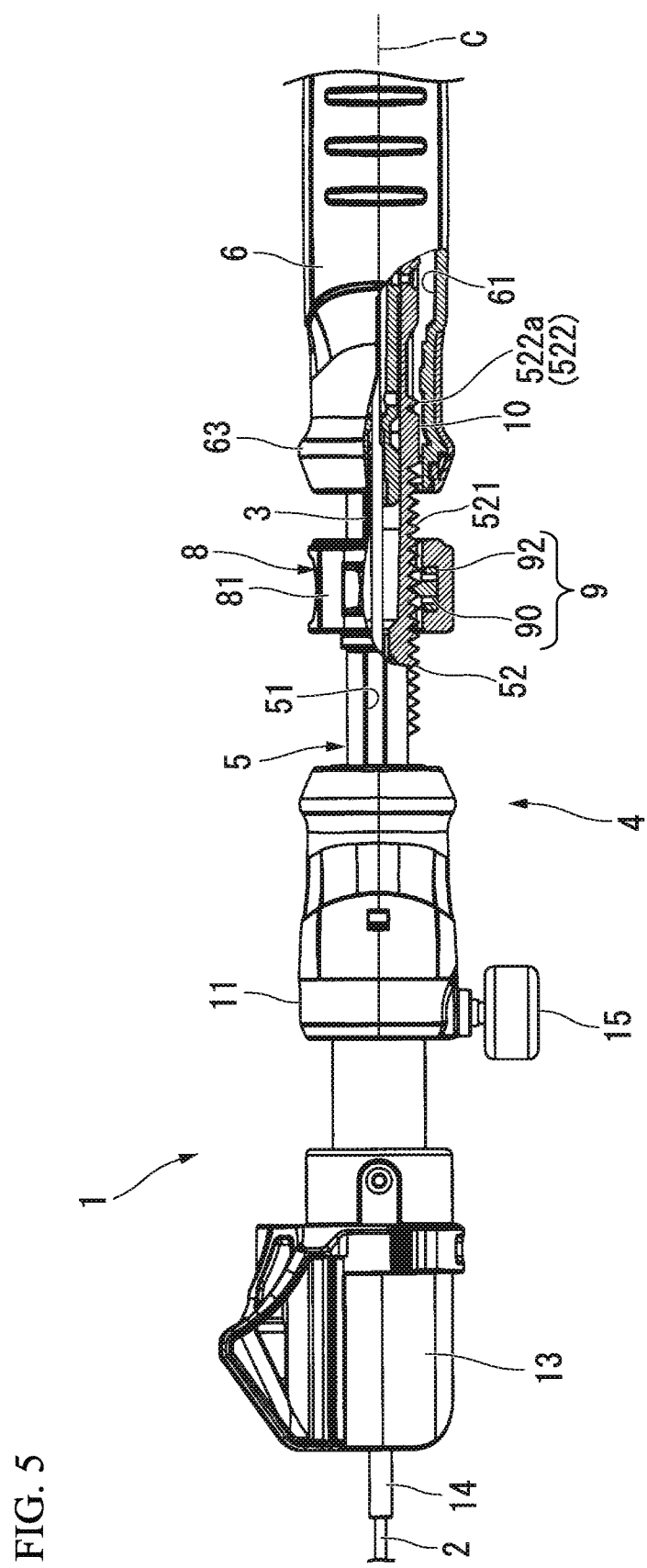
FIG. 5 is a partial cross-sectional view illustrating a manipulating unit of the endoscopic treatment tool according to the embodiment of the present invention.
Figure 6:
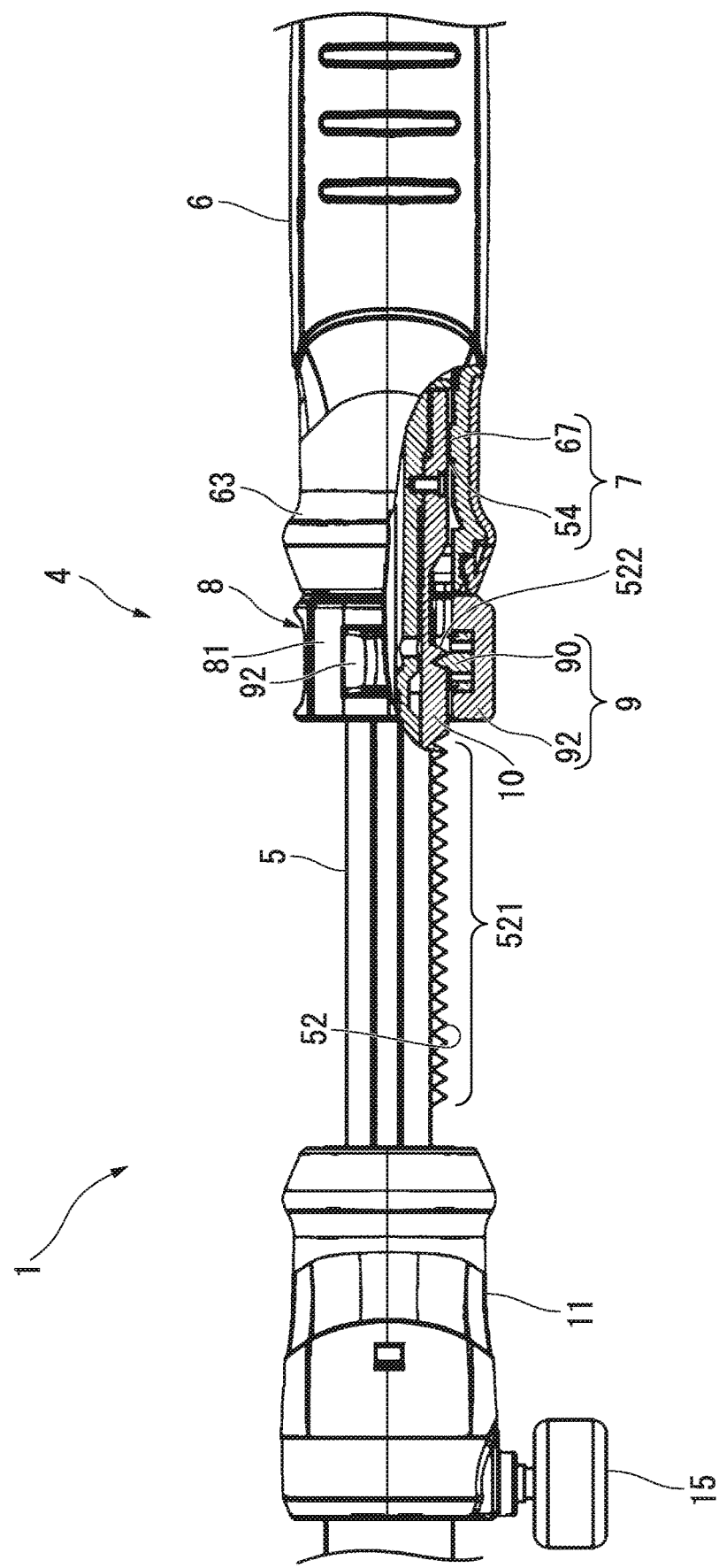
FIG. 6 is a partial cross-sectional view illustrating the manipulating unit of the endoscopic treatment tool according to the embodiment of the present invention.
Figure 7:
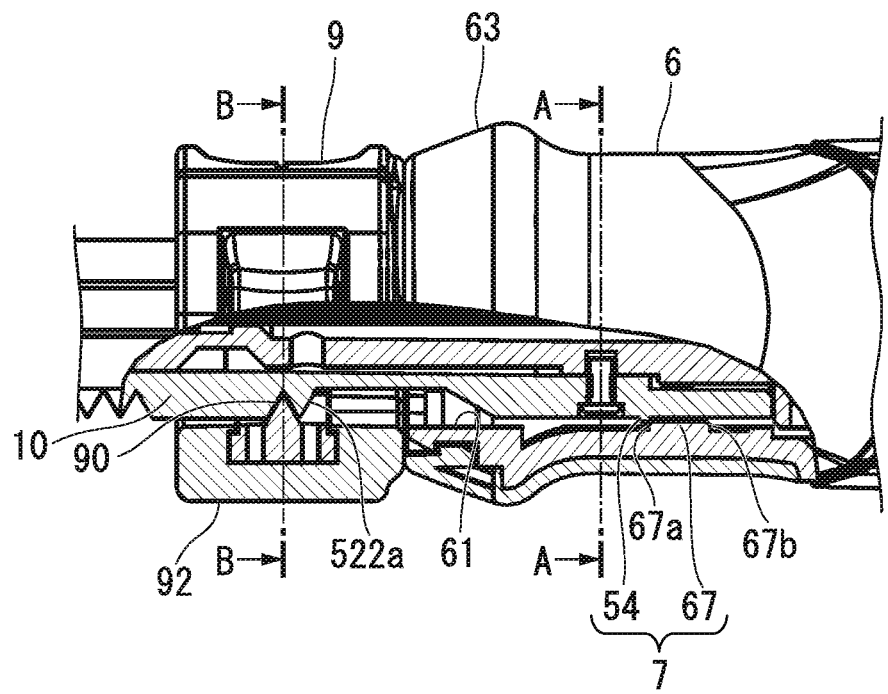
FIG. 7 is a partial cross-sectional view illustrating a first locking mechanism and a stopper according to the embodiment of the present invention.
Figure 8:
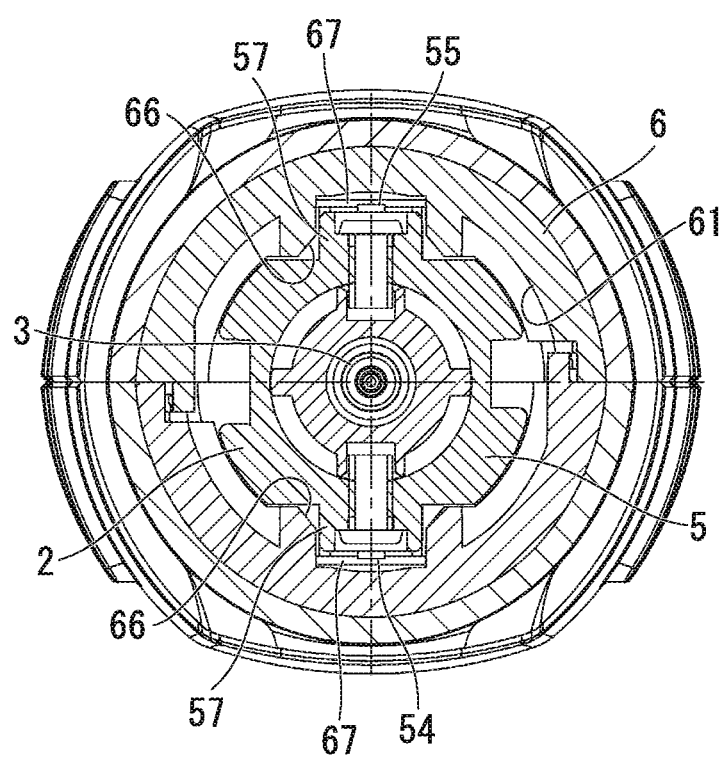
FIG. 8 is a cross-sectional view taken along line A-A in FIG. 7.

FIG. 2 is a bottom view illustrating the treatment tool 1. FIGS. 5 and 6 are partial cross-sectional views illustrating a manipulating unit 4 of the treatment tool 1. FIG. 5 illustrates the manipulating unit 4 in a state in which a distal end of a puncture needle 3 protrudes from a sheath 2. FIG. 6 illustrates the manipulating unit 4 in a state in which a distal end of the puncture needle 3 is accommodated in the sheath 2. FIG. 7 is an enlarged view of FIG. 6, which is a partial cross-sectional view of a distal end portion of a needle slider 6 and a stopper 8. FIG. 8 is a cross-sectional view taken along line A-A illustrated in FIG. 7.

As illustrated in FIG. 2, the treatment tool 1 includes a sheath 2, a puncture needle (treatment portion) 3, and a manipulating unit 4. The sheath 2 and the puncture needle 3 are provided over the entire length of the treatment tool 1, and the manipulating unit 4 is provided at the proximal end portion of the sheath 2 and the puncture needle 3.

The sheath 2 is an elongated tubular member having flexibility. The sheath 2 has an outer diameter that is capable of being inserted into a channel 107 of the endoscope 100. A lumen through which the puncture needle 3 is inserted is formed inside the sheath 2 over the entire length in the longitudinal direction. The sheath 2 is formed of a resin, a metal coil, or the like.

The puncture needle 3 is constituted by a needle tube of a hollow member. A distal end of the puncture needle 3 is formed to be inclined with respect to the central axis C and sharpened so that the distal end thereof is configured to be capable of being inserted into the living tissue. The puncture needle has flexibility and is made of a metal having elasticity that easily returns to a linear state even if it is bent by an external force.

The manipulating unit 4 includes a manipulation main body 5, a needle slider (a slider) 6, a first locking mechanism 7 (see FIG. 6), a stopper (a second locking mechanism) 8, a fixing mechanism 9, a restricting portion 10, and a sheath adjuster 11.

Figure 3:
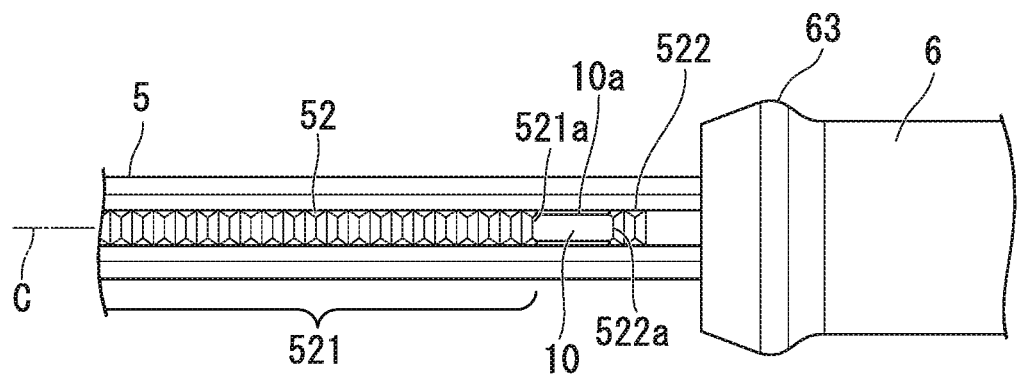
FIG. 3 is a bottom view illustrating a part of a manipulation main body of the endoscopic treatment tool according to the embodiment of the present invention.
Figure 4:
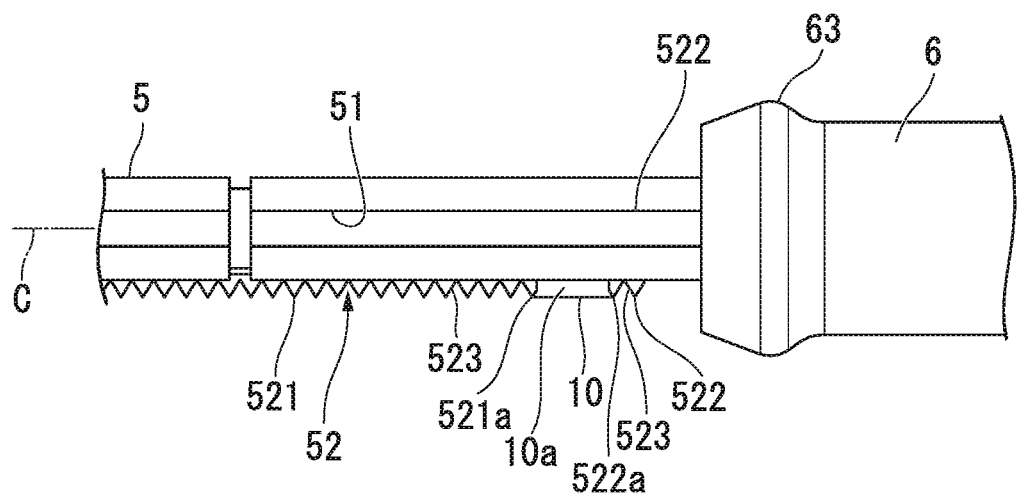
FIG. 4 is a side view illustrating a part of the manipulation main body of the endoscopic treatment tool according to the embodiment of the present invention.

FIG. 3 is a bottom view illustrating a part of the manipulation main body 5. FIG. 4 is a side view illustrating a part of the manipulation main body 5. The manipulation main body 5 is a tubular long shaft member formed of resin or the like. As illustrated in FIG. 4, two slider grooves 51 extending in parallel at positions symmetrical with respect to the central axis are formed on an outer peripheral surface of the manipulation main body 5.

As illustrated in FIGS. 3 and 4, a rack 52 is formed on the outer peripheral surface of the manipulation main body 5. A plurality of teeth extending in a direction orthogonal to the central axis C are formed to be lined in a direction of the central axis C to form the rack 52. The rack 52 and the slider groove 51 are disposed on the outer peripheral surface of the manipulation main body 5 so that the rack 52 is positioned between the two slider grooves 51.

The rack 52 includes a first region (a first fixing portion) 521 provided on the distal side and a second region (a second fixing portion) 522 provided on the proximal side. The first region 521 is longer than the second region 522 in the longitudinal direction. The restricting portion 10 is provided between the first region 521 and the second region 522. The restricting portion 10 is a protruding portion which connects a top portion of a tooth 521a provided on the most proximal end side of the first region 521 and a top portion of a tooth 522a provided on the most distal end side of the second region to extend in the longitudinal direction of the manipulation main body 5, and has a trapezoidal cross section orthogonal to the central axis C. The restricting portion 10 includes a wall portion (an abutting surface) 10a formed to protrude radially outward from the manipulation main body 5 from a concave portion (a bottom portion) of the teeth of the rack 52. The wall portion 10a is inclined from an upper surface (a surface farthest from the central axis C) of the restricting portion 10 toward the outer peripheral surface of the manipulation main body 5. The restricting portion 10 is configured such that a claw portion of a fixing mechanism to be described later is not capable of being engaged.

As illustrated in FIGS. 7 and 8, a pair of protrusions 54 and 55 are formed on the proximal end side of the manipulation main body 5. The pair of protrusions 54 and 55 are formed to protrude radially outward from the outer periphery of the manipulation main body 5. The first protrusion 54, which is one of the pair of protrusions 54 and 55, is provided on the proximal end side of the rack 52, and the other, the second protrusion 55, is provided symmetrical to the first protrusion 54 across the central axis C. A pair of guide convex portions 57 extending in the longitudinal direction are formed at a proximal end portion of the manipulation main body 5. The pair of protrusions 54 and 55 are formed in the pair of guide convex portions 57.

As illustrated in FIG. 5, a communication passage 61 extending in the direction of the central axis C is provided in the needle slider 6. The puncture needle 3 is inserted through the communication passage 61 over the entire length, and the puncture needle 3 and the needle slider 6 are fixed.

As illustrated in FIG. 8, a pair of guide grooves 66 are formed in the communication passage 61 of the needle slider 6 in the longitudinal direction. A convex portion 67 protruding toward the center of the needle slider 6 is formed at the bottom of each of the guide grooves 66. The first locking mechanism 7 is constituted by the convex portion 67 of the needle slider 6 and the protrusions 54 and 55 of the manipulation main body 5.

An enlarged diameter portion 63 having an outer diameter larger than that of the distal end of the needle slider 6 is formed at a distal end portion of the needle slider 6. The enlarged diameter portion 63 has a greater outer diameter than the proximal side and the distal side thereof such that an outer peripheral surface of the needle slider 6 is formed to bulge. The enlarged diameter portion 63 functions as a finger hook portion on which the operator hooks his or her finger when advancing and retracting the needle slider 6.

As illustrated in FIG. 2, a proximal end opening portion 62 is formed at a proximal end portion of the needle slider 6. An opening of a proximal end of the puncture needle communicates with the proximal end opening portion 62, and a stylet 64 (see FIG. 11) is insertable into the puncture needle from the proximal end opening portion 62. The proximal end opening portion 62 is configured to be capable of connecting a known syringe or the like, and is configured to be capable of suctioning an object inside the puncture needle.

Figure 9:
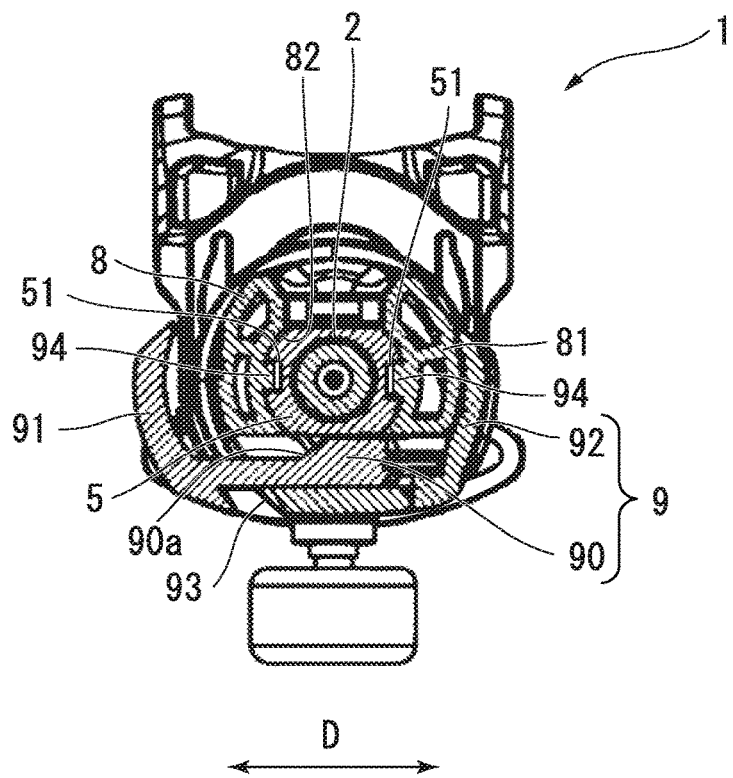
FIG. 9 is a cross-sectional view taken along the line B-B in FIG. 7.
Figure 10:
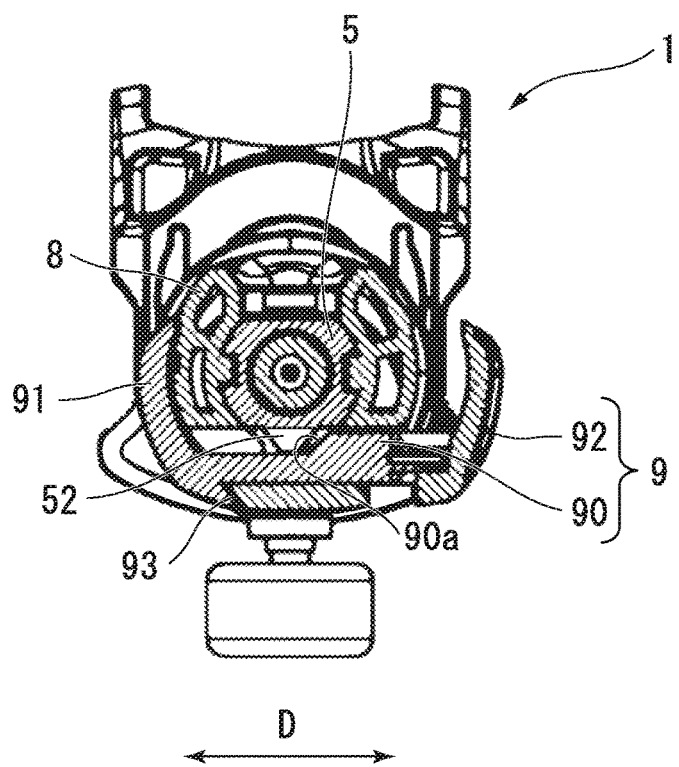
FIG. 10 is a cross-sectional view of the stopper according to the embodiment of the present invention.

As illustrated in FIG. 5, the stopper 8 includes a substantially cylindrical stopper main body 81 and a fixing mechanism 9. FIG. 9 is a cross-sectional view taken along line B-B illustrated in FIG. 7. FIG. 10 is a cross-sectional view illustrating the fixing mechanism 9 in the fixing release state in the same cross section as FIG. 9. A pair of protruding portions 94 that is insertable into the slider groove 51 of the manipulation main body 5 are formed in a lumen of the stopper main body 81 in the direction of the central axis C.

The fixing mechanism 9 is attached to the stopper main body 81 so as to be slidable with respect to the stopper main body 81 in the direction orthogonal to the central axis C. As illustrated in FIGS. 7 and 9, a claw portion (claw) 90 capable of engaging with a rack of the manipulation main body 5 is formed in the fixing mechanism 9. The claw portion 90 is formed in a convex shape corresponding to the shape of the concave portion of the teeth of the rack 52. Further, as illustrated in FIGS. 9 and 10, an end portion 90a of the claw portion 90 on the slide button 91 side is inclined downward in FIGS. 9 and 10, and has a tapered shape in which the thickness in the direction orthogonal to the central axis C gradually decreases.

The fixing mechanism 9 includes a pair of slide buttons 91 and 92 on both sides across the central axis C. The first slide button 91 of the pair of slide buttons 91 and 92 and the claw portion 90 are integrally formed, and in the other, the second slide button 92, a pressing portion 93 which presses the first slide button 91 is provided. The pair of slide buttons 91 and 92 are configured to be slidable in the direction orthogonal to the central axis C (a direction indicated by an arrow D in FIGS. 9 and 10).

As described above, the rack 52 has the first region 521 and the second region 522. The first region 521 is set so that the distal end of the puncture needle 3 protrudes from the sheath 2. When the claw portion 90 of the fixing mechanism 9 is engaged with the most proximal tooth in the first region 521, the distal end of the puncture needle 3 slightly protrudes from a distal end of the sheath 2. On the other hand, when the claw portion 90 is engaged with the teeth of the second region 522, the distal end of the puncture needle 3 is configured to be positioned and accommodated at the proximal end side by a predetermined distance or more from the distal end of the sheath 2.

Since the restricting portion 10 is formed in the wall portion 10a without forming the teeth of the rack 52, the restricting portion 10 is unengageable with the claw portion 90. Therefore, the restricting portion 10 is a part at which the stopper 8 is incapable of being fixed with respect to the manipulation main body 5. The restricting portion 10 is set in accordance with a positional relationship between the manipulation main body 5 and the needle slider 6 when the distal end of the puncture needle 3 is accommodated in the sheath 2 and the distance from the distal end of the sheath 2 to the distal end of the puncture needle 3 is within a predetermined range. As described above, since the end portion 90a of the claw portion 90 has a tapered shape, when the wall portion 10a of the restricting portion 10 and the end portion 90a of the claw portion 90 come in to line contact with each other, and the claw portion 90 comes into contact with the restricting portion 10, the force applied to the end portion 90a of the claw portion 90 and the restricting portion 10 is dispersed. Thus, the regulating force of the end portion 90a of the claw portion 90 and the restricting portion 10 is improved.

In the present embodiment, an example in which the restricting portion 10 has a trapezoidal cross section orthogonal to the central axis C is illustrated. However, the shape of the restricting portion 10 is not limited thereto, and the restricting portion 10 may be a quadrangular prism-shaped protruding portion having a rectangular cross section orthogonal to the center axis C.

Specifically, when the sheath 2 is bent due to the bending or meandering of the channel 107, in some cases, a relative position between the puncture needle 3 and the sheath 2 in the direction of the central axis C may change. Further, in some cases, due to dimensional errors that can occur during manufacture, errors may occur between the relative position of the puncture needle 3 to the sheath 2, and the relative position of the manipulation main body 5 to the needle slider 6. Under the influence of such factors, even when the distal end of the puncture needle 3 is designed to be positioned closer to the proximal side than the distal end of the sheath 2, in some cases, the puncture needle 3 may protrude from the distal end of the sheath 2. However, in the treatment tool 1 according to the present embodiment, the restricting portion 10 is provided to inhibit the stopper 8 from being positioned between the first region 521 and the second region 522 of the rack 52. As a result, it is possible to secure a state in which the puncture needle 3 is reliably accommodated in the sheath 2.

The sheath adjuster 11 is a tubular member, and the distal end of the manipulation main body 5 is inserted through the sheath adjuster 11. As illustrated in FIG. 2, a slide lock 12 attachable to detachable from the proximal end mouth ring 108 of the endoscope 100 is provided at a distal end portion of the sheath adjuster 11. Concavities and convexities are provided on the outer peripheral surface of the sheath adjuster 11 so that the operator can easily grip the sheath adjuster 11. A fixing screw 15 is attached to the sheath adjuster 11.

A holder 13 is provided on the distal side of the slide lock 12. The holder 13 is fixed to the sheath adjuster 11. The distal end side of the manipulating unit 109 (see FIG. 1) of the endoscope 100 is disposed in the holder 13.

The sheath 2, the puncture needle 3, the manipulation main body 5, the needle slider 6, the stopper 8 and the sheath adjuster 11 of the treatment tool 1 are configured as follows.

The puncture needle 3 is inserted into the manipulation main body 5, and the proximal end portion of the puncture needle 3 and the needle slider 6 are fixed. The manipulation main body 5 and the proximal end of the sheath 2 are fixed. The proximal end portion of the manipulation main body 5 is inserted into the communication passage 61 from a distal end side of the needle slider 6. The needle slider 6 is configured to be capable of advancing and retracting in the direction of the central axis C with respect to the manipulation main body 5. Since the needle slider 6 advances and retracts while the guide convex portion 57 of the manipulation main body 5 slides in the guide groove 66, the position of the needle slider 6 in the circumferential direction with respect to the manipulation main body 5 is fixed.

The needle slider 6 is provided to adjust a position of the puncture needle 3 with respect to the sheath 2. The puncture needle 3 is configured to advance and retract with respect to the sheath 2 in accordance with advance and retract manipulation of the needle slider 6 with respect to the manipulation main body 5.

In the first locking mechanism 7, the positional relationship between the protrusions 54 and 55 and the convex portion 67 is set so that the protrusions 54 and 55 of the manipulation main body 5 are positioned on the proximal end portion 67b side of the convex portion 67 when the distal end of the puncture needle 3 is in the position accommodated in the sheath 2. In the first locking mechanism 7, the protrusions 54 and 55 of the manipulation main body 5 abut a distal end portion 67a of the convex portion 67 with sliding of the needle slider 6 toward the proximal side. When the needle slider 6 is manipulated to further slide to the proximal side, the needle slider 6 slightly bends outward in the radial direction due to the pressing force between the protrusions 54 and 55 and the convex portion, and the protrusion passes over the convex portion. When the needle slider 6 slides until the protrusion reaches the proximal side of the convex portion, the pressing force on the bent needle slider 6 is released, the needle slider 6 slightly vibrates to generate a sound, and a click feeling occurs. The operator can recognize that the needle slider 6 has reached the temporary fixing position without looking at the manipulating unit, and that the distal end of the puncture needle 3 is accommodated in the sheath 2 by hearing the click or feeling it with his or her hand which grasps the needle slider 6. In order to more clearly generate the click feeling, it is more preferable that both end portions in the direction of the central axis C of the convex portion may be formed in a square shape.

As illustrated in FIG. 9, in the stopper 8, the manipulation main body 5 is inserted into a lumen 82 formed along the central axis C of the stopper main body 81. As illustrated in FIG. 2, the stopper 8 is capable of advancing and retracting in the direction of the central axis C with respect to the manipulation main body 5, and is provided on more distal side than the needle slider 6. The stopper 8 is provided for regulating the advanced position of the needle slider 6 with respect to the manipulation main body 5. Since the pair of protruding portions 84 slide in the slider groove 51 when the stopper 8 advancing and retracting with respect to the manipulation main body 5, a position of the stopper 8 in the circumferential direction with respect to the manipulation main body 5 is fixed.

In the present embodiment, the fixing mechanism 9 is configured to cause the slide buttons 91 and 92 to slide in a direction orthogonal to the central axis C (a direction of an arrow D illustrated in FIGS. 9 and 10), thereby switching a state in which the stopper 8 is fixed to the manipulation main body 5 and a state of releasing the fixing. In a state in which the claw portion 90 is engaged with the concave portion 523, the movement of the stopper 8 with respect to the manipulation main body 5 is restricted.

By causing the slide buttons 91 and 92 to slide in a direction D orthogonal to the central axis C with respect to the stopper main body 81, the claw portion 90 moves in the direction of the arrow D illustrated in FIG. 9 to switch between a fixed state in which the claw portion 90 is engaged with the concave portion 523 of the teeth of the rack 52 (FIG. 9) and a fixing release state in which the engagement between the claw portion 90 and the concave portion 523 is released (FIG. 10).

An amount of force (second amount of force) which locks the stopper 8 to the manipulation main body 5 is greater than an amount of force amount (first amount of force) which locks the needle slider 6 to the manipulation main body 5 when the needle slider 6 is temporarily fixed to the manipulation main body 5 by the first locking mechanism 7. Therefore, even if engagement in the first locking mechanism 7 is released and the needle slider 6 moves to the distal side due to its own weight or the addition of an external force not intended by the operator, the needle slider 6 abuts on the stopper 8, and the movement of the needle slider 6 is restricted. As a result, the needle slider 6 is prevented from moving to more distal side from the predetermined position, and it is possible to maintain the state in which the distal end of the puncture needle 3 is accommodated in the sheath 2.

The sheath adjuster 11 is provided for adjusting a protruding length of the sheath 2 from the channel 107. The position of the sheath adjuster 11 with respect to the manipulation main body 5 is fixed by the fixing screw 15, and the protruding length of the sheath 2 from the channel 107 is fixed.

A support pipe 14 protrudes from the distal end portion of the sheath adjuster 11. A distal end portion of the support pipe 14 is inserted into the channel 107 when the treatment tool 1 is attached to the endoscope 100. The support pipe 14 is inserted into the manipulation main body 5. The sheath 2 is inserted into the support pipe 14, and the proximal end portion of the sheath 2 protrudes from a proximal end of the support pipe 14 and is fixed to the manipulation main body 5.

Figure 11:
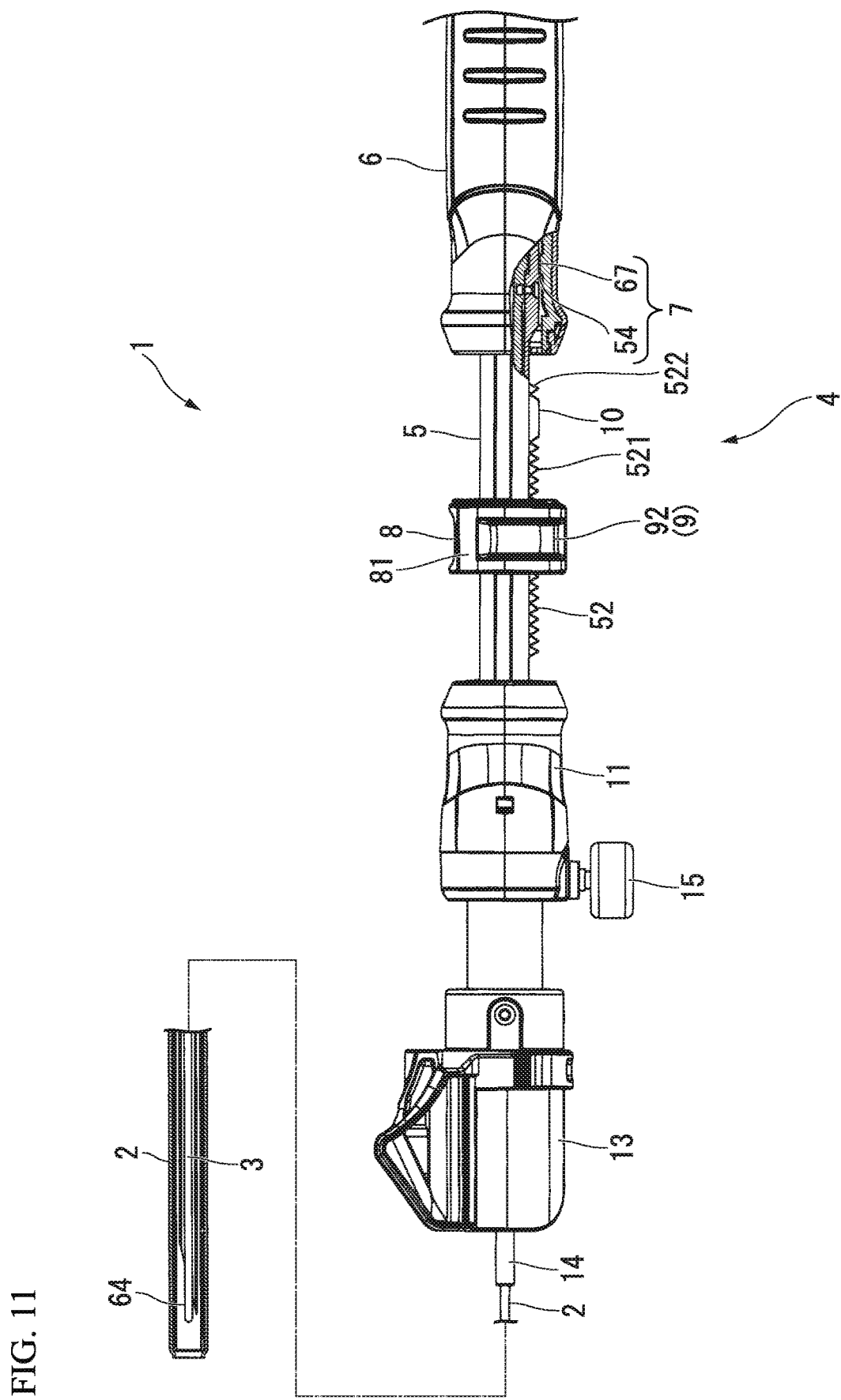
FIG. 11 is a diagram illustrating the operation of the endoscopic treatment tool according to the embodiment of the present invention.
Figure 12:
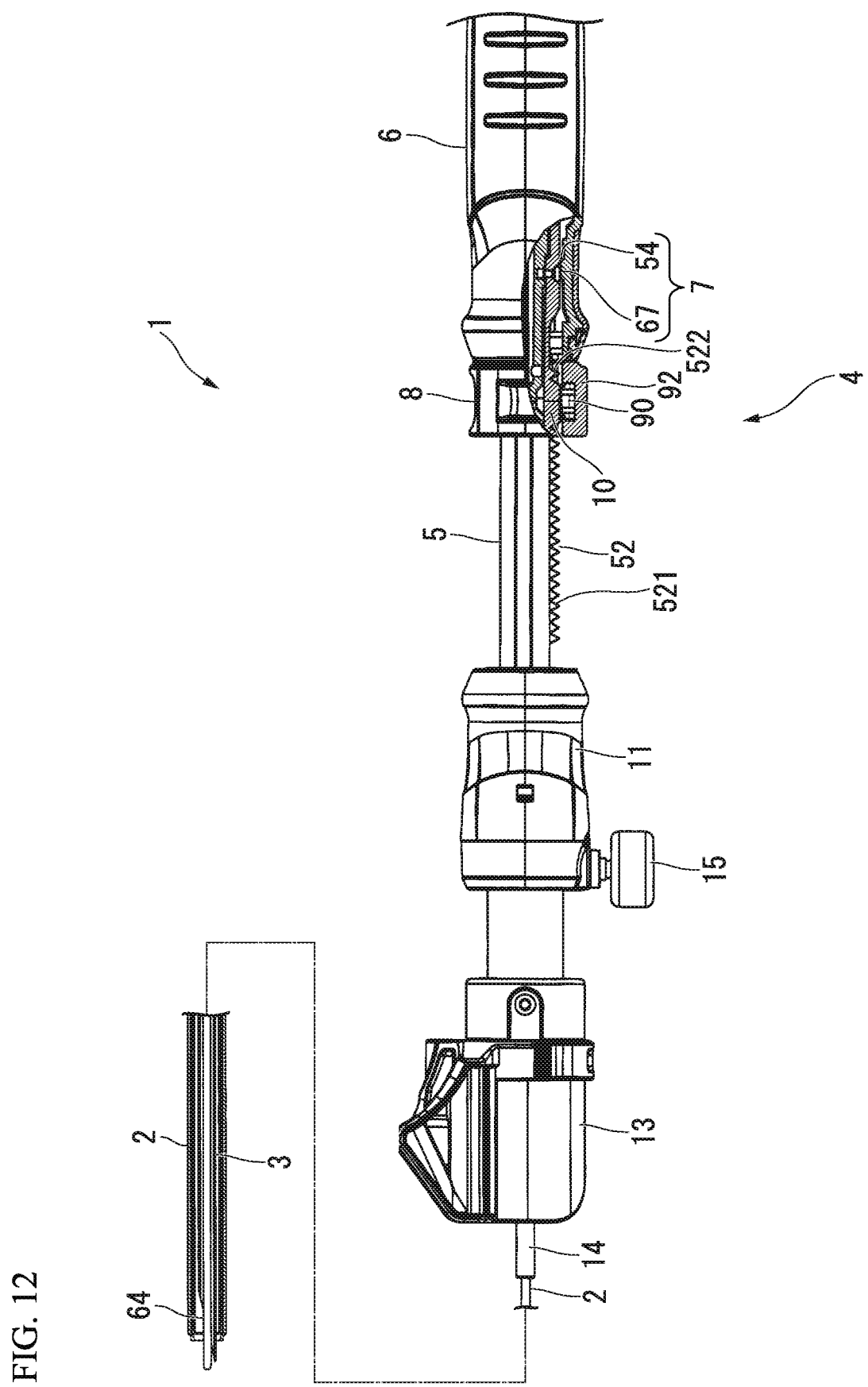
FIG. 12 is a diagram illustrating the operation of the endoscopic treatment tool according to the embodiment of the present invention.
Figure 13:
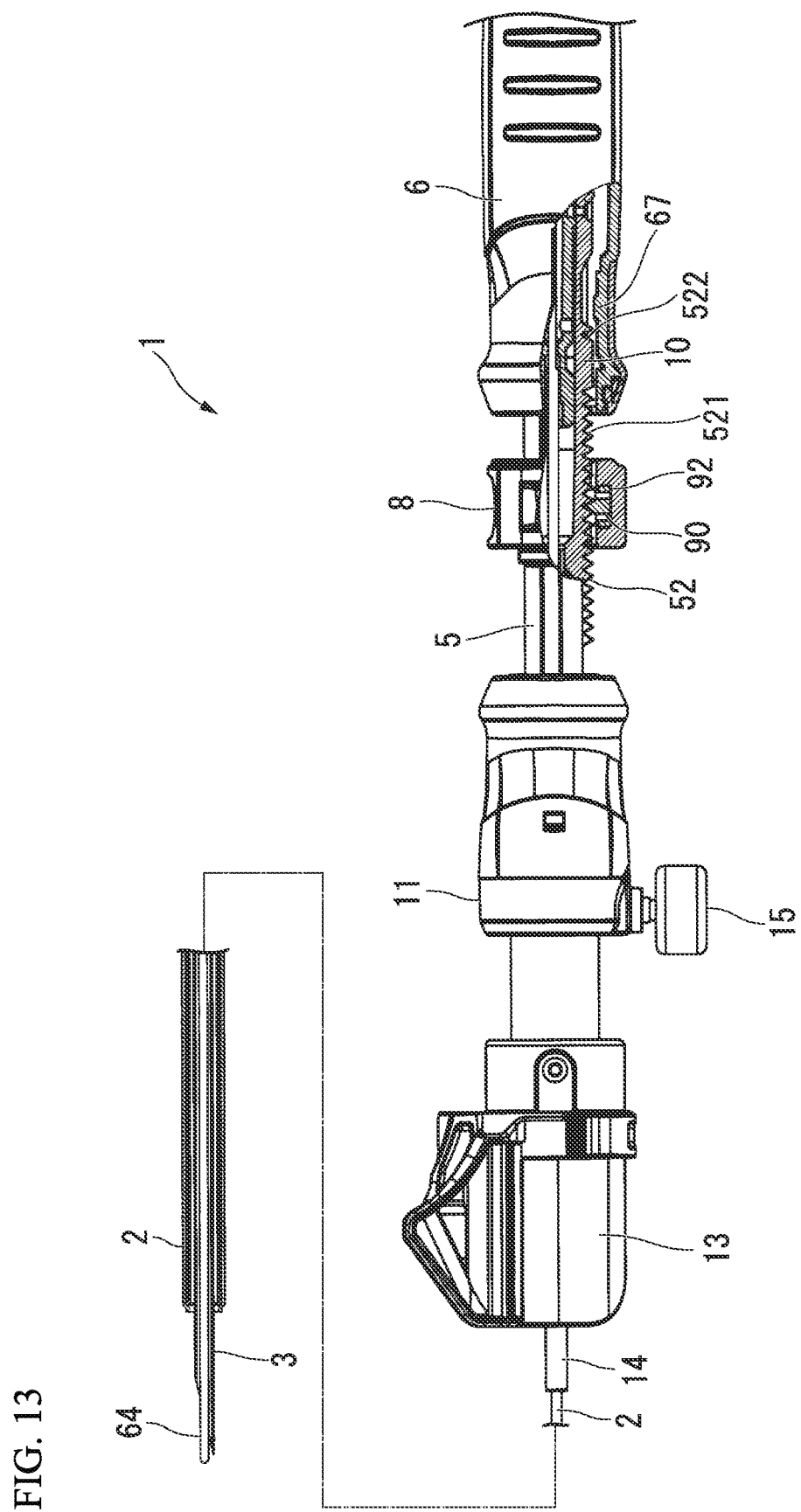
FIG. 13 is a diagram illustrating the operation of the endoscopic treatment tool according to the embodiment of the present invention.

Next, the operation of the treatment tool 1 according to the present embodiment at the time of usage will be described with reference to FIGS. 11 to 13. FIGS. 11 to 13 illustrate the sheath 2 and the puncture needle 3 at the distal end in an enlarged manner to illustrate a relationship between the positional relationship between the sheath 2 and the puncture needle 3 and the form of the manipulating unit 4. First, the endoscope 100 is inserted into the body cavity of a patient by a known procedure and advanced to the vicinity of the biopsy target tissue T to be collected or the target organ.

The operator performs a manipulation of holding a finger on the enlarged diameter portion 63 of the needle slider 6 and pulling the needle slider 6 toward the proximal side. As illustrated in FIG. 11, when the needle slider 6 is pulled toward the proximal side by a predetermined amount or more, the protrusions 54 and 55 of the manipulation main body 5 abut on the distal end portion 67a of the convex portion 67 of the needle slider 6, and the operator feel resistance at the time of pulling. When the operator performs the manipulation of further pulling the needle slider 6 toward the proximal side, since the protrusions 54 and 55 ride on the convex portion 67, the distal end portion of the needle slider 6 slightly bends. Thereafter, when the protrusions 54 and 55 climb over the convex portion 67 and reach more proximal side than the proximal end portion 67b of the convex portion 67, the pressing force to the needle slider 6 due to the protrusions 54 and 55 is released and the bending of the needle slider 6 is released. The needle slider 6 is locked to the manipulation main body 5 by the first locking mechanism 7. At this time, the needle slider 6 slightly vibrates, and a sound is generated to generate the click feeling, and the operator senses the click feeling on the hand for grasping the needle slider 6. Upon sensing the click feeling, the operator recognizes that the needle slider 6 moves toward the proximal side by a predetermined amount and the distal end of the puncture needle 3 is accommodated in the sheath 2.

Further, the manipulation of moving the needle slider 6 to the proximal side by holding the finger on the enlarged diameter portion 63 is not limited to the pulling manipulation, and it may be a manipulation of pushing the enlarged diameter portion 63 toward the distal side with the hand, depending on the method in which the operator holds the needle slider 6.

Next, the operator performs a manipulation of fixing the stopper 8 to the second region 522. The operator performs a manipulation of moving the stopper 8 toward the proximal end side with respect to the manipulation main body 5. The stopper 8 is moved to the proximal end side up to a position at which the stopper 8 abuts on the distal end of the needle slider 6, and the first slide button 91 is caused to slide in the direction D orthogonal to the central axis C to lock the claw portion 90 to the second region 522.

At this time, as illustrated in FIG. 12, when the claw portion 90 is positioned in the restricting portion 10, the claw portion 90 abuts on the wall portion 10a and even if the operator manipulates the first slide button 91, the first slide button 91 is immovable. As a result, the operator can recognize that the stopper 8 is in a position where the stopper 8 cannot be fixed, by manipulation of the first slide button 91. Therefore, the operator further moves the needle slider 6 to the proximal side to lock the claw portion 90 in the second region 522 as illustrated in FIG. 13.

When the claw portion 90 is locked in the second region 522, advance of the needle slider 6 is restricted, and a state in which the distal end of the puncture needle 3 is reliably accommodated in the sheath 2 is maintained. For example, even when the locking state of the first locking mechanism 7 is released by the own weight of the needle slider 6 and the needle slider 6 advances, the advance of the needle slider 6 is restricted by abutting the needle slider 6 on the stopper 8, thereby it is possible to prevent the distal end of the puncture needle 3 from protruding from the sheath 2.

Subsequently, the operator inserts the treatment tool 1 into the channel 107, inserts the holder 13 into the proximal end channel port 102, causes the slide lock 12 to slide in the direction orthogonal to the central axis C and engages the slide lock 12 with the proximal end channel port 102, thereby fixing the manipulating unit 4 to the endoscope 100. At this time, since a state in which the distal end of the puncture needle 3 is reliably accommodated in the sheath 2 is maintained, the interior of the channel 107 is not damaged by the puncture needle 3, and the treatment tool 1 is capable of being smoothly inserted into the channel 107.

Next, the protrusion length of the sheath 2 from the channel 107 is adjusted. The operator loosens the fixing screw 15, and advances the sheath adjuster 11 with respect to the manipulation main body 5, while observing the sheath 2 and the inside of the body by an optical imaging mechanism (not illustrated) and an ultrasonic scanning mechanism 104 provided in the endoscope 100, thereby adjusting the amount of protrusion of the sheath 2 from the distal end of the channel 107 to an appropriate amount. The fixing screw 15 penetrates the sheath adjuster 11 and is fitted into a screw hole (not illustrated) provided in the manipulation main body 5. When the fixing screw 15 is tightened against the manipulation main body 5, the sheath adjuster 11 is pressed against the manipulation main body 5 to fix the sheath adjuster 11 to the manipulation main body 5 in a non-slidable manner.

Next, the operator presses the second slide button 92 of the stopper 8 in the direction D orthogonal to the central axis C, and releases the fixing of the stopper 8 with respect to the manipulation main body 5. When the first slide button 91 is pushed to release the locking between the claw portion 90 and the second region 522, the fixing of the stopper 8 with respect to the manipulation main body 5 is released.

Next, as illustrated in FIG. 13, the operator moves the stopper 8 to the distal end side with respect to the manipulation main body 5, adjusts the amount of protrusion of the puncture needle 3 with respect to the sheath 2 to a desired amount of protrusion, and presses the slide button 91 to fix the slide button 91 to the teeth of the first region 521. As a result, the distal end of the puncture needle 3 enters a state capable of protruding from the sheath 2. At this time, a scale (not illustrated) provided in the manipulation main body 5 may be referred to.

Subsequently, the operator presses the enlarged diameter portion 63 of the needle slider 6 to the distal side and advances the needle slider 6 up to a position at which the needle slider 6 comes into contact with the stopper 8. As a result, the distal end of the puncture needle 3 is inserted into the biopsy target tissue T. The puncture needle 3 exposed from the surface of the biopsy target tissue T can be observed by the optical imaging mechanism, and the distal end portion of the puncture needle 3 inserted into the biopsy target tissue T can be observed by the ultrasonic scanning mechanism 104. At this time, it is possible to adopt a configuration in which the puncture needle 3 is punctured into the tissue at high speed by a known automatic puncture mechanism.

Next, the operator extracts the stylet 64 from the puncture needle 3. Thereafter, a known syringe is fixed to the proximal end opening portion 62, and the tissue collected in the distal end portion of the puncture needle 3 is suctioned and collected.

When the necessary amount of tissue can be collected, the needle slider 6 is retracted to the proximal side with respect to the manipulation main body 5, and the distal end of the puncture needle 3 is accommodated in the sheath 2. Specifically, the operator pulls the enlarged diameter portion 63 of the needle slider 6 toward the proximal side, and moves the needle slider 6 to the proximal side. When the needle slider 6 is pulled by a predetermined amount or more, the needle slider 6 is locked to the manipulation main body 5 by the first locking mechanism 7. At this time, as described above, a click feeling occurs and the operator can recognize that the distal end of the puncture needle 3 is sufficiently accommodated in the sheath 2.

Subsequently, the operator retracts the stopper 8 to the proximal end side until the stopper 8 comes into contact with the distal end of the needle slider 6, causes the first slide button 91 to slide in the direction D orthogonal to the central axis C, and locks the second region 522 and the claw portion 90. As a result, a state in which the distal end of the puncture needle 3 is accommodated in the sheath 2 is maintained.

Subsequently, the slide lock 12 is removed from the proximal end channel port 102 of the endoscope 100, and the treatment tool 1 is extracted from the channel 107. At this time, since the distal end of the puncture needle 3 is reliably accommodated in the sheath 2, the interior of the channel 107 is not damaged by the puncture needle 3, and the treatment tool 1 is capable of being smoothly extracted from the channel 107. Finally, the endoscope 100 is extracted from the patient and a series of manipulations is completed.

According to the treatment tool 1 according to the present embodiment, the needle slider 6 is temporarily fixed at the position at which the distal end of the puncture needle 3 is accommodated in the sheath 2 by the first locking mechanism 7, and the advance of the needle slider 6 is capable of being restricted by the stopper 8. As a result, it is possible to prevent the needle slider 6 from advancing at an unintended timing and the distal end of the puncture needle 3 from protruding from the distal end of the sheath 2 in two stages.

In the first locking mechanism 7, since the click feeling occurs when the needle slider 6 moves to the temporary fixing position, the operator can recognize that the distal end of the puncture needle 3 are accommodated in the sheath 2 by their ears and the feeling of the grasped needle slider 6.

Further, since the stopper 8 is capable of locking the needle slider 6 with the second amount of force greater than the first amount of force for locking the needle slider 6 in the first locking mechanism 7, for example, even when the locking of the needle slider 6 due to the first locking mechanism 7 is released by the own weight of the needle slider 6, the advance of the needle slider 6 is capable of being reliably restricted by the stopper 8.

Since the treatment tool 1 includes the fixing mechanism 9 that is capable of fixing the stopper 8 to the manipulation main body 5 by sliding with respect to the manipulation main body 5, the operator can fix the stopper 8 to the manipulation main body 5 by a simple manipulation. In the treatment tool 1 according to the present embodiment, since the fixing mechanism 9 has a configuration in which the claw portion 90 is movable by the slide button, the operator can switches between the fixed state and the fixing release state of the stopper 8 by the manipulation of pressing one of a pair of slide buttons with a finger grasping the manipulating unit 4. Therefore, it is possible to perform fixing or fixing release of the stopper 8 to the manipulation main body 5 with a simple manipulation.

Since the treatment tool 1 is provided with the restricting portion 10 between the first region 521 and the second region 522, the stopper 8 is not locked from the state in which the distal end of the puncture needle 3 is positioned at an approximately equal to the distal end of the sheath 2 to a state in which the distal end of the puncture needle 3 is securely accommodated in the sheath 2. Therefore, when the operator moves the stopper 8 toward the proximal end side from the first region 521, the stopper 8 cannot be fixed by the restricting portion 10, and when moving the stopper 8 to the second region 522 on the proximal end side from the restricting portion 10, the stopper 8 can be fixed to the manipulation main body 5. As a result, it is possible to prevent the position of the puncture needle 3 with respect to the sheath 2 from being fixed in a state in which the distal end of the puncture needle 3 protrudes from the sheath 2 due to factors such as bending of the sheath 2 or size error in manufacturing.

According to the treatment tool 1 according to the present embodiment, by including the first locking mechanism 7, the stopper 8, and the restricting portion 10, when the needle slider 6 and the stopper 8 are locked at the proximal end side, the distal end of the puncture needle 3 is in a state of being reliably accommodated in the sheath 2. Therefore, the operator can recognize that the distal end of the puncture needle 3 is reliably accommodated in the sheath 2 without visually checking the manipulating unit 4, and it is possible to improve manipulating property.

In the present embodiment, the fixing mechanism 9 has a configuration in which the claw portion 90 is movable by the slide buttons 91 and 92 as an example, but the fixing mechanism 9 is not limited to this configuration. For example, the stopper main body may fix to the manipulation main body by causing a screw that is capable of being fitted into a concave portion formed on the outer peripheral surface of the manipulation main body 5 to slide (for example, to be screwed) from the radially outer side of the stopper toward the central axis C. However, when the slide buttons 91 and 92 are adopted, the operator can switch between the fixed state and the fixing release state, only by performing the slide manipulation of the slide button slide with the finger of the hand grasping the manipulating unit 4. Therefore, the operator can manipulate with one hand, manipulation of visual observation is not necessary, and the manipulating property is excellent.

In the present embodiment, the example in which the distal end of the needle slider 6 abuts on the proximal end of the stopper 8 when the stopper 8 is locked in the second region is described, but the configuration of the endoscopic treatment tool is not limited thereto. The stopper 8 may be able to restrict the advance of the needle slider 6 when the first locking mechanism 7 is released. In a state in which the needle slider is locked by the first locking mechanism 7, the distal end of the needle slider 6 and the proximal end of the stopper 8 may not abut on each other.

In the present embodiment, an example in which the first locking mechanism 7 is configured by the two convex portions 67 and the two protrusions 54 and 55 is illustrated. However, the number of convex portions and the number of protrusions is not limited thereto, and at least one set or more of first locking mechanisms may be provided between the manipulation main body 5 and the needle slider 6.

In the present embodiment, as the first locking mechanism 7, the configuration in which the convex portion 67 and the protrusions 54 and 55 are engaged with each other is illustrated, but the configuration of the first locking mechanism 7 is not limited thereto. For example, the first locking mechanism 7 may be configured so that an O-ring is attached to the outer periphery of the manipulation main body 5, the O-ring abuts on the communication passage of the needle slider, the inner diameter of the communication passage is changed by the relative position between the needle slider and the manipulation main body 5, and a press-fitted state between the O-ring and the communication passage changes.

While the embodiments of the present invention have been described above, the technical scope of the present invention is not limited to the above-described embodiments, and it is possible to change the combination of constituent elements in each embodiment, add various changes to each constituent element, or delete them within the scope that does not depart from the gist of the present invention.

What is claimed is:

1. An endoscopic treatment tool, comprising:
a sheath inserted into a treatment tool insertion channel of an endoscope;
a treatment portion inserted into the sheath, the treatment portion being configured to protrude from and retract into a distal end of the sheath;
a manipulation main body fixed to a proximal end of the sheath, the manipulation main body being formed along a longitudinal axis of the sheath, and the manipulation main body having a rack in which a plurality of teeth are arranged along the longitudinal axis;
a slider configured to advance and retract in a longitudinal axis direction relative to the manipulation main body, the slider being configured to cause the treatment portion to protrude from and retract into the sheath;
a first locking mechanism configured to lock the slider relative to the manipulation main body at a position at which a distal end of the treatment portion is accommodated in the sheath in accordance with a retracting manipulation of the slider;
a second locking mechanism provided at a further distal side than the first locking mechanism, the second locking mechanism being configured to advance and retract in the longitudinal axis direction relative to the manipulation main body, the second locking mechanism being further configured to restrict advance of the slider by being locked to the manipulation main body;
a fixing mechanism provided in the second locking mechanism, the fixing mechanism having a claw configured to engage with the plurality of teeth of the rack to fix a position of the second locking mechanism relative to the manipulation main body; and
a restricting portion having an abutting surface formed to protrude radially outward from the manipulation main body from a concave portion of the rack, the restricting portion being provided at the manipulation main body, the restricting portion being configured to restrict fixing of the fixing mechanism relative to the manipulation main body.

2. The endoscopic treatment tool according to claim 1, wherein a distal end of the slider abuts the second locking mechanism in a state in which the slider is locked by the first locking mechanism.

3. The endoscopic treatment tool according to claim 1, wherein the rack has a first fixing portion and a second fixing portion, the second fixing portion being positioned at a proximal end part of the rack, the first fixing portion being positioned at a distal side of the second fixing portion,
- the second locking mechanism being configured to be fixed by the claw by sliding of the claw through one of the first fixing portion and the second fixing portion, and
- the abutting surface being positioned between the first fixing portion and the second fixing portion.

4. The endoscopic treatment tool according to claim 3, wherein the first fixing portion is formed in a region in which the slider is located so that the distal end of the treatment portion protrudes from the distal end of the sheath, and
- the second fixing portion is formed in a region in which the slider is located so that the distal end of the treatment portion is accommodated in the sheath.

5. The endoscopic treatment tool according to claim 3, wherein the first fixing portion and the second fixing portion are formed by the plurality of teeth, the plurality of teeth having a plurality of concavities, each of which being provided between adjacent teeth of the plurality of teeth,
- the claw engages with the concavities by moving relative to the concavities, and
- the abutting surface protruding further outward in a radial direction of the manipulation main body than the concavities.

6. The endoscopic treatment tool according to claim 1, wherein the slider is fixed to the treatment portion and the slider is provided in the manipulation main body.

7. The endoscopic treatment tool according to claim 1, wherein
- the manipulation main body includes protrusions protruding radially outward of the sheath,
- the slider includes a convex portion protruding radially inward of the sheath,
- the protrusions and the convex portion comprise the first locking mechanism.

8. A handle configured to be manipulated by an operator in an endoscopic treatment tool, the endoscopic treatment tool including a sheath inserted into a treatment tool insertion channel of an endoscope, and a treatment portion configured to protrude from and retract into a distal end of the sheath, the handle comprising:
- a manipulation main body fixed to a proximal end of the sheath, the manipulation main body being formed along a longitudinal axis of the sheath, the manipulation main body having a rack in which a plurality of teeth are arranged along the longitudinal axis;
- a slider configured to advance and retract relative to the manipulation main body, the slider being configured to cause the treatment portion to protrude from and retract into the sheath by advancing and retracting;
- a first locking mechanism configured to lock the slider relative to the manipulation main body at a position at which a distal end of the treatment portion is accommodated in the sheath in accordance with a retract manipulation of the slider;
- a second locking mechanism provided on a further distal side than the first locking mechanism, the second locking mechanism being configured to advance and retract in the longitudinal axis direction relative to the manipulation main body, the second locking mechanism being further configured to restrict advance of the slider by being locked to the manipulation main body;
- a fixing mechanism provided in the second locking mechanism, the fixing mechanism having a claw configured to engage with the plurality of teeth of the rack to fix a position of the second locking mechanism relative to the manipulation main body; and
- a restricting portion having an abutting surface formed to protrude radially outward from the manipulation main body from a concave portion of the rack, the restricting portion being provided at the manipulation main body, the restricting portion being configured to restrict fixing of the fixing mechanism relative to the manipulation main body.

9. The handle according to claim 8, wherein a distal end of the slider abuts the second locking mechanism in a state in which the slider is locked by the first locking mechanism.

10. The handle according to claim 8, wherein the rack has a first fixing portion and a second fixing portion, the second fixing portion being positioned at a proximal end part of the rack, the first fixing portion being positioned at a distal side of the second fixing portion,
- the second fixing portion being configured to be fixed by the claw by sliding of the claw through one of the first fixing portion and the second fixing portion, and
- the abutting surface being positioned between the first fixing portion and the second fixing portion.

11. The handle according to claim 10, wherein the first fixing portion is formed in a region in which the slider is located so that the distal end of the treatment portion protrudes from the distal end of the sheath, and
- the second fixing portion is formed in a region in which the slider is located so that the distal end of the treatment portion is accommodated in the sheath.

12. The handle according to claim 10 wherein the first fixing portion and the second fixing portion are formed by the plurality of teeth, the plurality of teeth having a plurality of concavities, each of which being provided between adjacent teeth of the plurality of teeth,
- the claw engages with the concavities by moving relative to the concavities, and
- the abutting surface protruding further outward in a radial direction of the manipulation main body than the concavities.

13. The handle according to claim 8, wherein the slider is fixed to the treatment portion and the slider is provided in the manipulation main body.

14. The handle according to claim 8, wherein
- the manipulation main body includes protrusions protruding radially outward of the sheath,
- the slider includes a convex portion protruding radially inward of the sheath,
- the protrusions and the convex portion comprise the first locking mechanism.

\* \* \* \* \*